United States Patent [19]

Mai

[11] Patent Number: 4,907,967
[45] Date of Patent: Mar. 13, 1990

[54] PARAOCCLUSIVE DENTAL INSTRUMENT

[76] Inventor: Martin Mai, Büttnergasse 1, A-1232 Vienna, Austria

[21] Appl. No.: 268,946

[22] Filed: Nov. 8, 1988

[30] Foreign Application Priority Data

Nov. 10, 1987 [AT] Austria ................................. 2967/87

[51] Int. Cl.$^4$ ............................................. A61C 19/64
[52] U.S. Cl. ................................................... 433/73
[58] Field of Search ...................... 433/73, 32, 37, 75, 433/76

[56] References Cited

U.S. PATENT DOCUMENTS

| | | |
|---|---|---|
| 1,589,973 | 6/1926 | Landa ..................................... 433/73 |
| 2,832,137 | 4/1958 | Moore et al. ......................... 433/73 |
| 3,069,774 | 12/1962 | Levey et al. . | 
| 4,306,861 | 12/1981 | Dickson .................................. 433/73 |

*Primary Examiner*—Robert Peshock
*Attorney, Agent, or Firm*—Spencer & Frank

[57] ABSTRACT

A paraocclusive instrument including two holding jaws laterally applied to the lower dental arch and a basic element in communication with the holding jaws in the form of a rod to transfer movement of the lower jaw to display and/or recording devices. The holding jaws are pivotally connected with pivot arms which are pivotally mounted at the basic element and extend divergingly from this bearing position at the basic element to the connecting points with the holding jaws. A lockable adjustment device is provided at the basic element for setting the mutual position of the pivot arms. The adjustment device includes a rod mounted at or in the basic element which is longitudinally displaceable and articulated to the pivot arms to positively control them and which, if displaced longitudinally, pivots the pivot arms. It is advantageous for the end of the rod facing the pivot arms to be connected with the pivot arms by guide arms. It is further desirable that the basic element be configured as a tube and the rod be displaceably mounted in this tube. The end of the rod remote from the pivot arms projects out of the tubular basic element and is provided with a thread onto which a nut is threaded when the rod is pushed axially into the tube, it forms a stop which lies at the end of the tube. The pivot arms are bent at right angles in the elevational direction and the individual components of the instrument are composed of a high strength light metal, preferably of titanium.

17 Claims, 1 Drawing Sheet

PARAOCCLUSIVE DENTAL INSTRUMENT

BACKGROUND AND DESCRIPTION OF THE PRIOR ART

The present invention relates to a paraocclusive dental instrument including two adjustable holding jaws to be attached to the lower dental arch and a basic element in communication with these holding jaws in the form of a rod or the like. The instrument is provided to transfer the movement of the lower jaw to display and/or recording devices.

In order to detect damage to the mandibular joint and to detect the movement behavior of the lower jaw with reference to the upper jaw during normal chewing, paraocclusive instruments are often employed to pick up the movement of the lower jaw. These are instruments equipped with holding jaws which, themselves, are fastened to the exterior of the lower dental arch by means of an adhesive and a compensating substance. The movement of the basic element of the paraocclusive instrument which follows the movement of the lower jaw is detected mechanically or electronically and is displayed and/or recorded, with a conclusion as to, for example, damage to the mandibular jaw or malocclusions or faulty tooth formations from such a visible display of the movement behavior. By application of the holding jaws of the instrument to the exterior of the lower dental arch, the influence emanating from this instrument due to contact between the teeth of the lower jaw and the teeth of the upper jaw in the plane or area of the occlusion is substantially suppressed and measurements can be made which are true-to-life during speaking or chewing.

Prior art paraocclusive instrument have been produced, analogously to dental prostheses, as individual specimens adapted to the shape of the lower dental arch of the respective patient and in which the holding jaws are combined with the basic element to form a one-piece structure. The manufacture of such paraocclusive instruments is very labor intensive which results not only in high costs but also requires undesirable waiting periods.

A paraocclusive instrument is known (ZWR-Das Deutsche Zahnarzteblatt [The German Dentist periodical]8/1987, page 702–704) which includes two sickle-shaped holding jaws that are combined into an arch which follows the lower dental arch, with outwardly projecting stubs being provided at the adjacent ends of the two holding jaws. These stubs are connected with one another by two parallel dual-thread screws which set the spacing and the mutual angular position of the two stubs and thus also set the holding jaws. One of these stubs is provided with an extending rod. Although this paraocclusive instrument can be adapted to various shapes and sizes of the lower jaw, the manipulations of both dual-thread screws required to accomplish this demand considerable skill since these two screws are disposed in the immediate vicinity of the holding jaw, which lies against the lower dental arch and since an adjustment of one the two dual-thread screws influences the other. Moreover, with the given shape of the holding jaws, in many cases it is possible to realize only a rough match to the shape of the dental arch. Thus, this prior art paraocclusive instrument is often adjusted on a model of the respective patient's lower jaw and an individual insert produced from a preliminary impression is attached to the interior of the holding jaws so that the use of this prior art instrument, in spite of its adjustability, is still very labor intensive.

SUMMARY OF THE INVENTION

It is an object of the present invention to provide a paraocclusive instrument which has a simple structure, is easily adjusted and can be employed for a large number of patients without the need for labor intensive individual adaptation.

According to the invention, the paraocclusive instrument of the above-mentioned type is characterized in that the holding jaws are pivotally connected approximately in their center with pivot arms which, in turn, are pivotally mounted at the basic element and extend divergingly from this bearing location at the basic element toward the points of connection with the holding jaws. A fixable adjustment device is provided at the basic element to engage the pivot arms and adjust the position of the pivot arms relative to one another.

With this configuration, the above-mentioned objective can easily be realized. The pivotal connection of the holding jaws with the pivot arms which, in turn, are pivotally mounted at the basic element, results in a good seat of the holding jaws and thus of the paraocclusive instrument at the lower dental arch which can be realized through the intermediary of adhesive or compensating masses. A lockable adjustment device is provided which engages the pivot arms and with which the position of the pivot arms relative to one another can be set, thus simplifying adaptation of the paraocclusive instrument to the dimensions and shape of the respective patient's lower dental arch since the presence of the pivot arm makes it possible to arrange the adjustment device at an easily accessible location and since the pivotal connection of the holding jaws with the pivot arms permits automatic alignment of the holding jaws with the outer shape of the lower dental arch. Thus, a good seat and hold of the paraocclusive instrument at the lower dental arch can be realized by means of an easy and quickly performed setting manipulation so as to permit accurate detection in the static and dynamic domain in conformance with reality of movements of the lower jaw produced by the muscles intended for lower jaw movement and of externally guided lower jaw movements. Thus it is possible in a simple manner to examine the state and function of the mandibular jaws and to detect the possible presence of teeth which interfere with the movement of the lower jaw and/or the function of the mandibular jaws due to their shape or position.

This results in a structurally very simple configuration and also simple operation of the adjustmen device if a provision is made that the adjustment device include a rod which is longitudinally displaceably mounted at the basic element and is articulated to the pivot arms so as to positively control them and pivot the pivot arms when it is longitudinally displaced. This results in a very stable configuration of the articulated connection of the rod with the pivot arm if the end of the rod facing the pivot arms is connected with the pivot arms by way of guide arms. If the rod is provided with a thread accommodating a nut provided for setting the axial position of this rod, preferably at its end remote from the pivot arms, this permits, in a structurally simple manner, the realization of an adjustability which is easily operated and is accurate.

The arrangement of the thread at the end of the rod remote from the pivot arms, with such end generally projecting from the patient's mouth, permits further simplification of the operation of the paraocclusive instrument. Another solution results here, which is very simple with respect to its structure, if the basic element is given a tubular configuration and the rod is mounted so as to be displaceable in this tube. Moreover, based on this solution, a particularly advantageous embodiment can be realized if the end of the rod remote from the pivot arms projects from the tubular basic element and a nut is screwed onto this end. When the rod is pushed axially into the tube, the nut forms a stop which comes to lie at the end of the tube.

Regarding the displacement movements and displacement forces to be transferred from the adjustment device to the pivot arms which are pivotally mounted at the basic element, in order to adjust the holding jaws, it is advantageous to provide the pivot arms in the form of two-armed levers with the holding jaws pivotally mounted at one of their ends and the other end being hinged to the adjustment device.

To be able to realize the most normal lip closure possible without interference and a substantially natural lip position for lower jaw movement and chewing processes to be examined, a fact that has great significance for uninterfered with analysis of the movement of the lower jaw, it is preferred that the pivot arms be bent at right angles in the elevational axis or, in other words, in a direction parallel to the geometric axis of their pivoting movement and, thus, the holding jaws, when the instrument is inserted in the mouth, lie lower than the basic element projecting from the mouth. In this way, the basic element of the paraocclusive instrument can project from the mouth at a location at which the lips contact on another when the mouth is naturally closed. Thus it is possible to unimpededly analyze lower jaw movements occurring during speaking and singing as well as the lower jaw movements occurring during chewing, with the possibility in the latter case to close the lips without difficulty.

In order for the weight and mass of the paraocclusive instrument to interfere as little as possible with or change the lower jaw movement to be examined, which likewise is of significance for the analysis of lower jaw movements during speaking, singing and chewing, it is advantageous if the individual parts of the instrument are made primarily of a high strength light metal, preferably of titanium. This configuration also makes it possible to produce the individual parts of the instrument in a relatively simple manner.

The invention will now be described in greater detail with reference to an embodiment thereof which is schematically illustrated in the drawing.

DESCRIPTION OF THE PREFERRED EMBODIMENT

Figure 1:
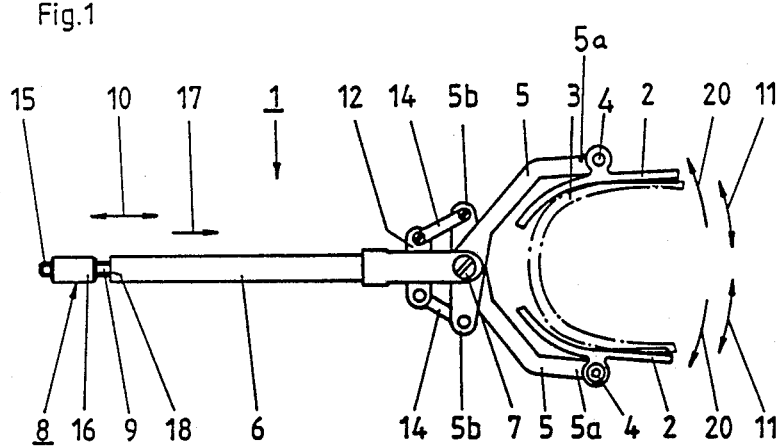
FIG. 1 is a plan view of a paraocclusive instrument configured according to the invention.
Figure 2:
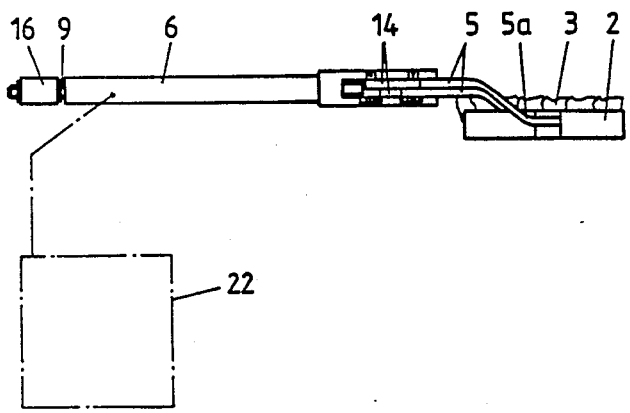
FIG. 2 is a side view of the instrument of FIG. 1.

In the embodiment of a paraocclusive instrument 1 according to the invention, as shown in FIGS. 1 and 2, two holding jaws 2 are provided which serve to fasten this instrument to the dental arch 3 of the lower jaw, shown in dashed lines in FIG. 1. Holding jaws 2 are pivotally connected with pivot arms 5 at pivot joints 4 disposed in the center of these holding jaws and pivot arms 5 in turn are pivotally mounted at the basic element 6 of the paraocclusive instrument. Mounting of pivot arms 5, which are configured as dual-arm levers, is here effected by means of a shaft 7 disposed at basic element 6. Pivot arms 5 extend divergingly from the bearing location at basic element toward the points of connection with holding jaws 2 formed by pivot joints 4. Pivot joints 4 at which holding jaws 2 are in pivotal communication with pivot arms 5, are disposed at one end 5a of pivot arms 5, which are configured as dual-arm levers; at the other end 5b of pivot arms 5, these pivot arms are connected with a fixable adjustment device with which the position of pivot arms 5 relative to one another and thus also the position of holding jaws 2 relative to one another can be set. Adjustment device 8 includes a rod 9 which is mounted so as to be displaceable in basic element 6 and which is articulated to pivot arms 5. When displaced longitudinally, this rod pivots pivot arms 5 in the sense of double arrows 11. For this purpose, the end 12 of rod 9 facing the pivot arms is connected with pivot arms 5 by way of guide arms 14 which engage at ends 5b of pivot arms 5. Basic element 6 is configured as a tube in which a rod 9 is displaceably mounted in a well protected arrangement. At the end remote from pivot arms 5, rod 9 is provided with a thread 15 on which a nut 16 is disposed to set the axial position of rod 9. If rod 9 is inserted axially into the tubular basic element 6 in the sense of arrow 17, nut 16 forms a stop which comes to lie at the end 18 of the tube.

If rod 9 is pushed into tube 6 in the sense of arrow 17, holding jaws 2 move away from one another and are pivoted outwardly by pivot arms 5 as shown by arrows 20. By appropriate displacement of nut 16, the insertion of rod 9 into tubular basic element 6 can be limited and thus also the degree of divergence of the holding jaw so that the total width of this instrument remains correspondingly limited, this being of significance for insertion into the mouth. By subsequent turning of nut 16 in the sense of pulling the end of rod 9 out of tubular basic element 6 in a direction opposite to arrow 17, holding jaws 2 can be moved toward one another and can be brought to lie against the sides of the lower dental arch, with an adhesive or compensating substance advisably being inserted between holding jaws 2 and lower dental arch 3.

As soon as paraocclusive instrument 1 is fastened to lower dental arch 3, with tubular basic element 6 projecting from the mouth, appropriate connection of basic element 6 with a recording or imaging device 22 will make visible and document the movement of the lower jaw.

If the paraocclusive instrument is to be removed again from the lower dental arch, it is merely necessary to remove nut 16 on thread 15 from the end 18 of tube 6 to the extent that it is possible again to push rod 9 into tube 6 in the sense of arrow 17, thus moving holding jaws 2 away from one another again and thus releasing them from lower dental arch 3.

As can be seen in FIG. 2, pivot arms 5 are bent at right angles in the elevational direction, i.e. in a direction parallel to the geometric axis of their pivoting movement, and thus, if the instrument is inserted into the mouth, holding jaws 2 lie lower than basic element 6 which protrudes from the mouth. Thus it is possible, if the paraocclusive instrument is inserted into the mouth, to keep the lips normally closed, even during movement of the lower jaw as it occurs, for example during the chewing process, and nevertheless ensure a movement sequence for the lower jaw which is substantially uninfluenced by the lips.

The individual components of instrument 1 are preferably composed of a high strength light metal, particularly titanium, because the low weight of the paraocclusive instrument makes it possible to ensure that this instrument does not cause any significant changes in jaw movement and additionally because it is possible to manufacture the individual components of the instrument substantially without problems from such a metal.

The invention now being fully described, it will be apparent to one of ordinary skill in the art that many changes and modifications can be made thereto without departing from the spirit or scope of the invention as set forth herein.

The present disclosure relates to the subject matter disclosed in Austrian patent Application A 2967/87 of Nov. 10th, 1987, the entire specification of which is incorporated herein by reference.

What is claimed is:

1. A paraocclusive instrument comprising, in combination:
   (a) two holding jaws laterally applicable to the lower dental arch;
   (b) a rod-shaped basic element in communication with said holding jaws to transfer movement of the lower jaw to display and/or recording devices;
   (c) pivot arms, said holding jaws being pivotally connected at a central region thereof to said pivot arms, said pivot arms also being pivotally mounted to said basic element and extending divergingly from the basic element to the pivotal connection with said holding jaws; and
   (d) lockable adjustment means at said basic element engaging said and serving to adjust the mutual position of the pivot arms.

2. A paraocclusive instrument as defined in claim 1, wherein the adjustment means includes a rod mounted at or in the basic element and longitudinally displaceable relative to said basic element, said adjustment means connected to the pivot arms in an articulated manner so as to positively control said pivot arms, said adjustment means, when longitudinally displaced, pivoting said pivot arms.

3. A paraocclusive instrument as defined in claim 2, wherein the end of the rod at said pivot arms is connected with the pivot arms by guide arms.

4. A paraocclusive instrument as defined in claim 2, wherein said rod is includes a thread at its end remote from said pivot arms, and a nut threadedly engaging said thread for setting the axial position of said rod.

5. A paraocclusive instrument as defined in claim 3, wherein said rod is includes a thread at its end remote from said pivot arms, and a nut threadedly engaging said thread for setting the axial position of said rod.

6. A paraocclusive instrument as defined in claim 2, wherein said basic element is configured as a tube and said rod is displaceable in said tube.

7. A paraocclusive instrument as defined in claim 3, wherein said basic element is configured as a tube and said rod is displaceable in said tube.

8. A paraocclusive instrument as defined in claim 4, wherein said basic element is configured as a tube and said rod is displaceable in said tube.

9. A paraocclusive instrument as defined in claim 5, wherein said basic element is configured as a tube and said rod is displaceable in said tube.

10. A paraocclusive instrument as defined in claim 6, wherein the end of said rod remote from said pivot arms projects from said tubular basic element and said nut is threaded onto said end whereby, if the rod is pushed axially into the tube, said nut forms a stop which is disposed at the end of the tube.

11. A paraocclusive instrument as defined in claim 9, wherein the end of said rod remote from said pivot arms projects from said tubular basic element and said nut is threaded onto said end whereby, if the rod is pushed axially into the tube, said nut forms a stop which is disposed at the end of the tube.

12. A paraocclusive instrument as defined in claim 1, wherein said pivot arms are configured as dual-arm levers, said holding jaws being pivotally mounted at one end thereof, the other ends thereof being articulatedly connected with said adjustment means.

13. A paraocclusive instrument as defined in claim 11, wherein said pivot arms are configured as dual-arm levers, said holding jaws being pivotally mounted at one end thereof, the other ends thereto being articulatedly connected with said adjustment means.

14. A paraocclusive instrument as defined in claim 1, wherein said pivot arms are bent at right angles in the direction parallel to the geometric axis of their pivoting movement, whereby, if the instrument is inserted into the mouth, the holding jaws lie lower than the basic element which projects from the mouth.

15. A paraocclusive instrument as defined in claim 13, wherein said pivot arms are bent at right anles in the direction parallel to the geometric axis of their pivoting movement, whereby, if the instrument is inserted into the mouth, the holding jaws lie lower than the basic element which projects from the mouth.

16. A paraocclusive instrument as defined in claim 1, wherein the individual components of said instrument are made of titanium.

17. A paraocclusive instrument as defined in claim 14 wherein the individual components of said instrument are made of titanium.

* * * * *